(12) United States Patent
Hewes et al.

(10) Patent No.: US 6,375,352 B1
(45) Date of Patent: Apr. 23, 2002

(54) APPARATUS AND METHOD FOR OBTAINING X-RAY TOMOSYNTHESIS DATA FOR MAMMOGRAPHY

(75) Inventors: Ralph Allen Hewes, Burnt Hills; Mehmet Yavuz, Clifton Park, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/409,889

(22) Filed: Oct. 1, 1999

(51) Int. Cl.[7] .................................................. H05G 1/30
(52) U.S. Cl. ...................... 378/196; 378/21; 378/22; 378/23; 378/37; 378/195; 378/197
(58) Field of Search .............................. 378/21, 22, 23, 378/37, 195, 196, 197

(56) References Cited

U.S. PATENT DOCUMENTS

| | | | |
|---|---|---|---|
| 5,386,447 A | * | 1/1995 | Siczek .......................... 378/37 |
| 5,651,004 A | | 7/1997 | Klotz, Jr. et al. |
| 5,654,997 A | | 8/1997 | Brownell et al. |
| 5,805,664 A | | 9/1998 | Whipple, III et al. |
| 5,872,828 A | * | 2/1999 | Niklason et al. .............. 378/23 |

OTHER PUBLICATIONS

Niklason et al., "Digital Tomosynthesis in Breast Imagin", Radiology, Vol. 205, No. 2, pp. 399–406 (1997).

* cited by examiner

Primary Examiner—Robert H. Kim
Assistant Examiner—Therese Barber
(74) Attorney, Agent, or Firm—Lester R. Hale; Donald S. Ingraham

(57) ABSTRACT

An apparatus and method are provided for obtaining x-ray tomosynthesis data desirable for mammography. The apparatus operates in conjunction with gravity to quickly and smoothly move an x-ray source through a plurality of positions relative to a stationary digital detector and a patient's breast to obtain a plurality x-ray images of the patient's breast which can then be processed for examination by a physician or radiologist. In one embodiment, an actuator such as a hydraulic system is operably connectable to the radiation source to controllably allow the radiation source to move under the influence of gravity from an elevated position to a lower position relative to the digital detector.

24 Claims, 4 Drawing Sheets

APPARATUS AND METHOD FOR OBTAINING X-RAY TOMOSYNTHESIS DATA FOR MAMMOGRAPHY

BACKGROUND OF THE INVENTION

This invention relates generally to mammography, and more particularly, to an apparatus and method for readily obtaining and processing tomosynthesis data for x-ray examination of a patient's breasts.

Mammography is a low-dose x-ray procedure that creates one or more images of a patient's breasts desirable for detection of early stages of cancer. FIG. 1 illustrates one example of a prior art mammography machine 10. Mammography machine 10 generally includes an x-ray tube 12 attached to an arm 14, which arm 14 is pivotally attached to a support 16, and a film plate 18 attached to an arm 20, which arm 20 is also pivotally attached to support 16. X-ray tube 12 and arm 14, and film plate 18 and arm 20, are counterbalanced so that x-ray tube 12 and film plate 18 may be easily manually pivoted, upwardly and downwardly, and locked in position at different angular orientations.

A typical mammography procedure takes approximately thirty minutes. The procedure generally includes obtaining two images of each of the patient's breasts, one from above and one from the side. For example, separate images are obtained of each of the patient's breasts with x-ray tube 12 and film plate 18 disposed in a vertically orientated arrangement along axis A (i.e., cranial-caudal) as shown in FIG. 1. In addition, separate images are obtained of each the patient's breasts with x-ray tube 12 and film plate 18 oriented on an angle, e.g., along axis B1 (i.e., medio-lateral oblique) for one of the patient's breasts, and along axis B2 for the patient's other breast.

During the procedure, the patient's breast is compressed between a compression paddle 22, e.g., a piece of plastic, and film plate 18 to flatten the breast making the breast easier to be imaged. In obtaining the images, either from above or from the side, x-ray tube 12 is aligned perpendicular or normal to film plate 18. A physician or radiologist then reviews the images of the breast, i.e., mammograms, to identify any breast cancer.

While the above described procedure is one of the best methods of detecting early forms of breast cancer, it is still possible for the detection of breast cancer to be missed by a physician or radiologist reviewing the mammograms. For example, breast cancer may be missed by being obscured by radiographically dense, fibroglandular breast tissue.

Tomosynthesis breast imaging, in which a plurality of images are acquired as the x-ray source is moved in an arc relative to a stationary digital detector, has been studied in an effort to detect early forms of breast cancer. By shifting and adding the plurality of images, it is possible to reconstruct any plane in the breast being imaged that is parallel to the detector.

Numerous drawbacks have prevented the widespread implementation of tomosynthesis breast imaging. For example, the procedure requires in combination, an x-ray source that limits x-ray exposure to the patient and a digital x-ray detector. Also, the procedure requires that the digital x-ray detector and the patient's breast be maintained in a stationary or fixed position while the x-ray tube is moved and positioned for obtaining the plurality of images.

Therefore, there is a need for an apparatus and method for implementing tomosynthesis breast imaging in which an x-ray source is quickly and smoothly moved and positioned relative to an x-ray detector to obtain a plurality of images of a patient's breast.

SUMMARY OF THE INVENTION

An apparatus and method are provided for obtaining tomosynthesis data of an object such as a patient's breast in which the apparatus includes a radiation source, a radiation detector, and an actuator operably connectable to the radiation source. The actuator is operable to controllably allow the radiation source to move under the influence of gravity from a first position to a second position relative to the radiation detector, wherein radiation emitted by the radiation source at a plurality of positions between the first position and the second position and passing through the object is detectable by the radiation detector.

DETAILED DESCRIPTION OF THE INVENTION

Figure 1:
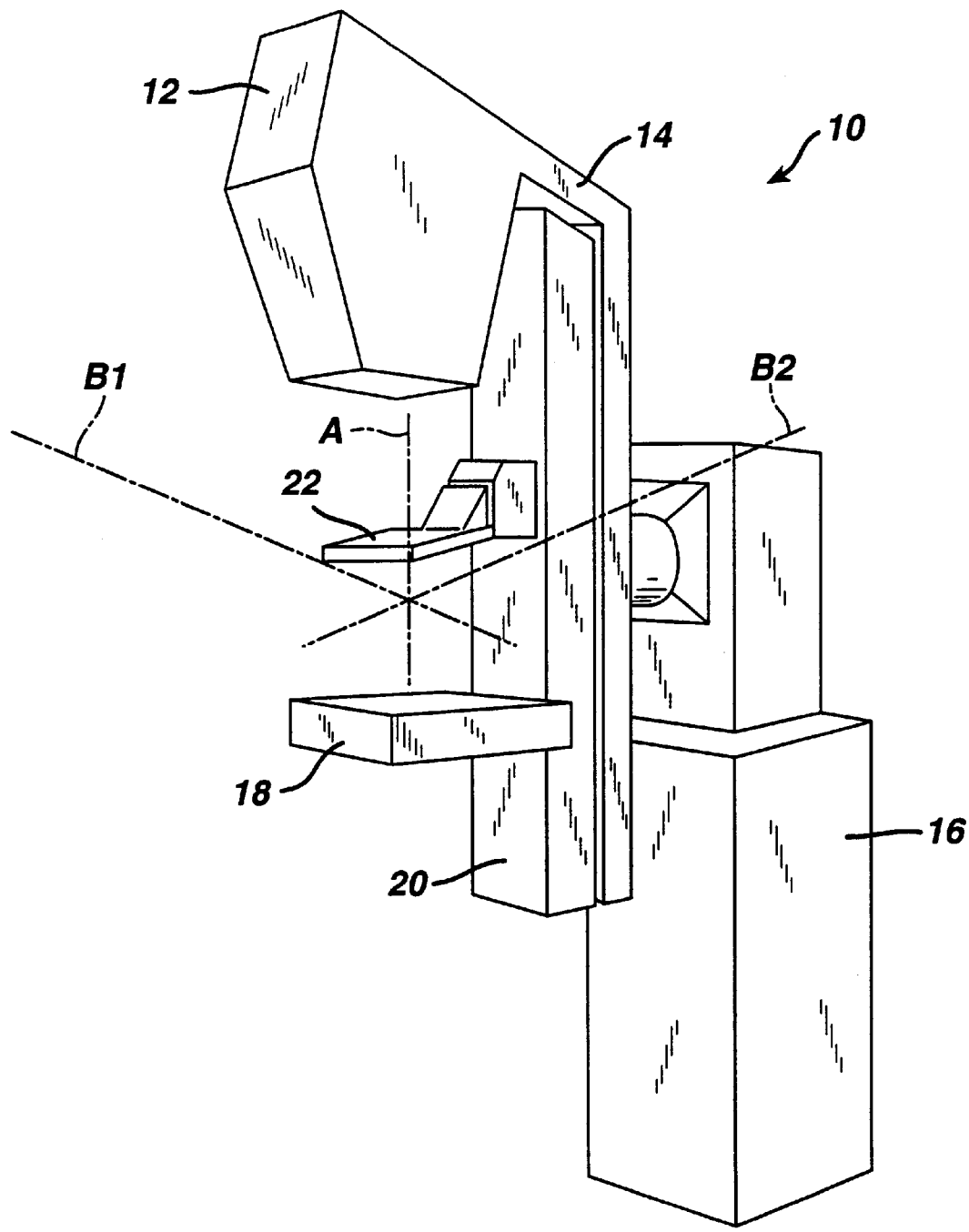
FIG. 1 is a perspective view of a prior art x-ray mammography machine.
Figure 2:
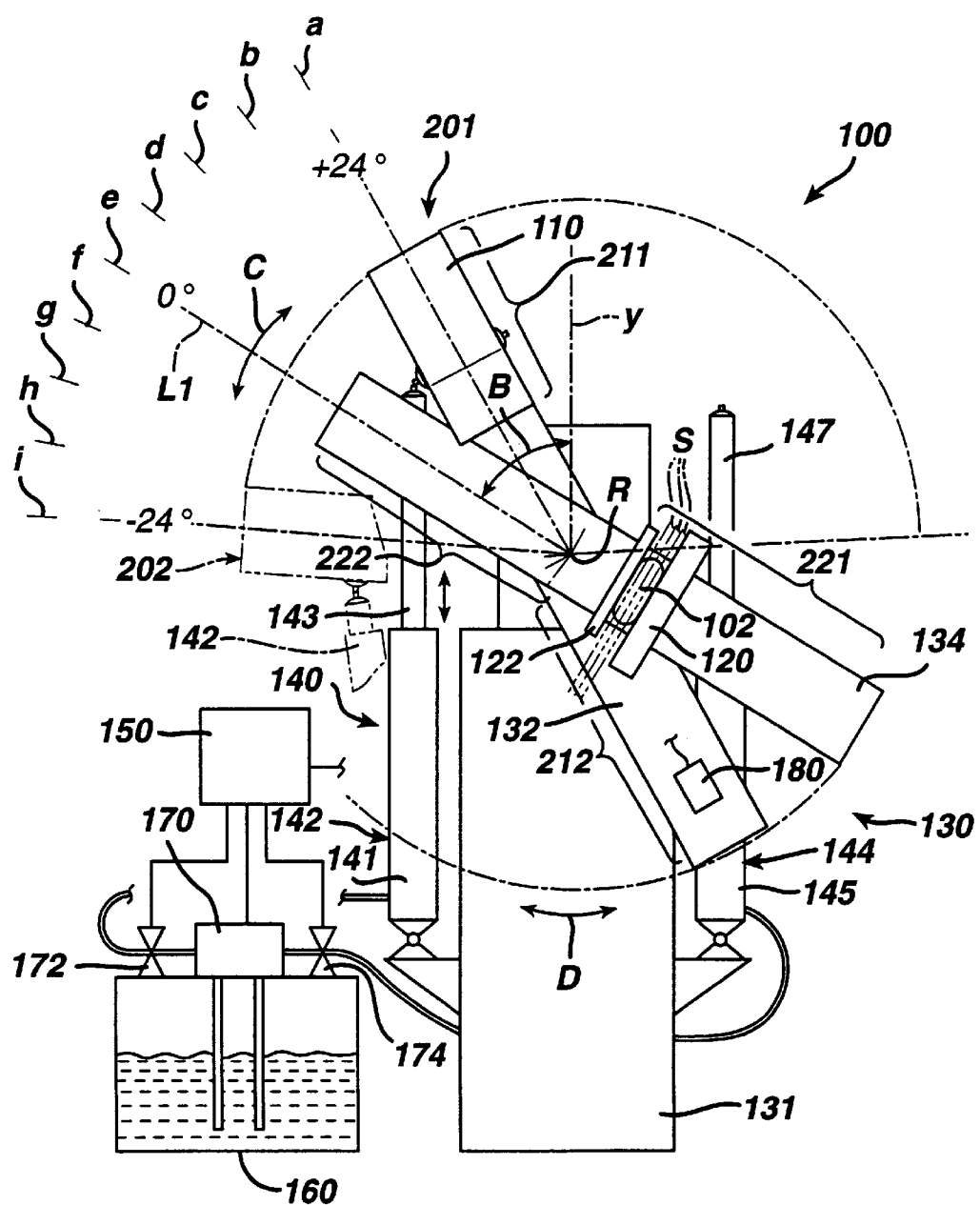
FIG. 2 is a diagrammatic, front elevational view of one embodiment of the present invention for an apparatus for obtaining tomosynthesis data of a patient's breast.
Figure 3:
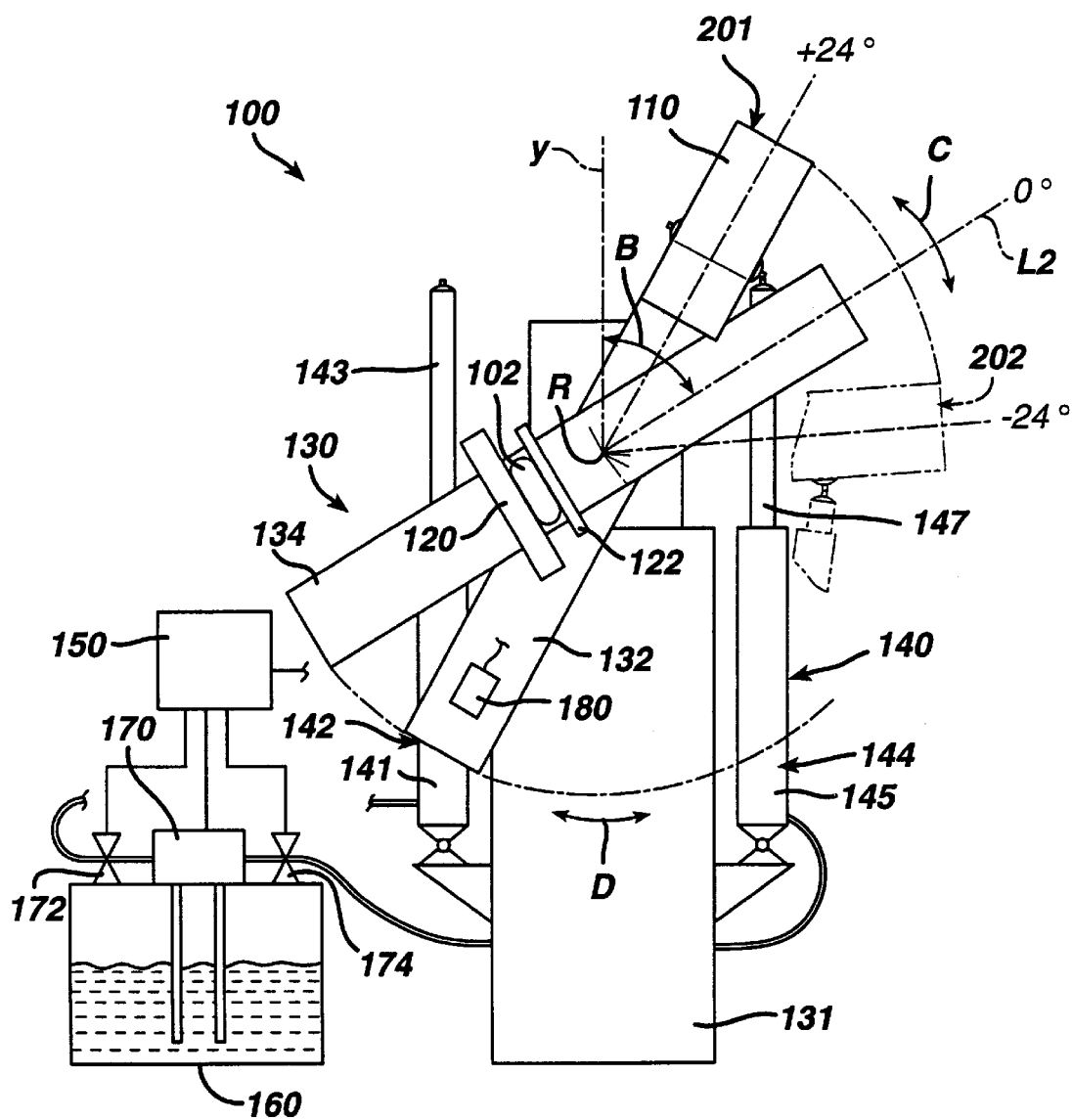
FIG. 3 is a diagrammatic, front elevational view of the apparatus, shown in FIG. 2, configured for obtaining tomosynthesis data of the patient's other breast.

An apparatus 100 according to the present invention for obtaining x-ray tomosynthesis data of an object 102 such as a patient's breast for early detection of cancer is illustrated in FIGS. 2 and 3. In this exemplary embodiment, the apparatus operates in conjunction with gravity to smoothly move a radiation source through a plurality of positions relative to a radiation detector and the patient's breast to obtain a plurality images of the patient's breast which can be processed for examination by a physician or radiologist.

In one aspect of the invention, the actuator is operable to control movement of the radiation source so that the radiation source stops at the plurality of positions and is operable to smoothly transition the radiation source between the plurality of positions. Desirably, the acceleration of the radiation source varies generally sinusoidally over time.

In another aspect of the invention, an arm having a first end portion is attached to the radiation source and a second end portion is pivotally attached to a support so that the radiation source is movable along an arc. A hydraulic system operably connectable to the arm controllably allows the radiation source to move under the influence of gravity from at least one elevated position to at least one lower position relative to the radiation detector, wherein radiation emitted from the radiation source at a plurality of positions between the at least one elevated position and the at least one lower position and passing through the object is detectable by the radiation detector. As used herein, "under the influence of gravity" and the like refers to gravity being the motive force for transitioning the x-ray source from one position to a next sequential position as the source is moved to obtain the desired tomosynthesis data. Further, as used herein, "operably connected" and the like refers to a coupling of components together to enable the components to provide a desired operation or movement; examples include, but are not limited to, mechanical coupling by means of fasteners (such as cotter pin couplings, spring release latches, and the like) that provide a detachable coupling between component parts.

In a further aspect of the invention, a method is provided for obtaining tomosynthesis data of an object in which the method comprises the steps of positioning a radiation source in an elevated position with the object disposed between the radiation source and a radiation detector, irradiating the object with radiation at a plurality of radiating positions as the radiation source is allowed to move under the influence of gravity from an elevated position to a lower position, and detecting radiation passing through the object at the plurality of positions with the radiation detector. Desirably, the method further includes the step of generating, from the detected radiation passing through the object at each of the plurality of positions, a plurality of spaced-apart planar images through the object.

Such an apparatus is simpler and more robust than, for example, a mammography machine with one or more servomotors, which are used to physically move and position the x-ray source relative to the digital detector. Such a motorized system imparts thrusting or jolting motions to the machine which affects the ability to maintain the detector and the patient's breast in a stationary or fixed position throughout the procedure. Advantageously, the apparatus according to the present invention limits abrupt thrusting or jolting motions throughout the apparatus, so that the detector and the patient's breast is better maintained in a stationary position throughout the procedure.

Exemplary apparatus 100 includes an x-ray source 110, a detector 120, and an actuator 130 for controllably allowing x-ray source 110 to move under the influence of gravity relative to detector 120. Actuator 130 includes a support 131, a first arm 132 (also referred to x-ray source arm) attached to support 131 and to x-ray source 110, a second arm 134 (also referred to as x-ray detector arm) attached to support 131 and to detector 120, and an actuating system 140.

X-ray source 110 is typically an x-ray tube and detector 120 is typically a digital x-ray detector. For example, detector 120 may be a solid state radiation imager, having e.g., a cesium iodide phosphor (scintillator) on an amorphous silicon transistor-photodiode array. Other suitable detectors may include one or more charge coupled devices (CCD) or a direct digital detector which converts x-rays directly to digital signals. While detector 120 is illustrated as being flat and defining a flat image plane, other configurations of digital x-ray detectors may be suitably employed, e.g., a curved-shaped digital x-ray detector having a curved image plane.

X-ray source 110 and detector 120 are separately movable relative to each other. For example, arm 132 has a first end 211 or portion attached to x-ray source 110 and a second end 212 or portion pivotally attached to support 131 so that x-ray source 110 is rotatable about a point or axis R in the directions indicated by curved double-headed arrow C. Similarly, arm 134 has a first end 221 or portion attached to detector 120 and a second end 222 or portion pivotally attached to support 131 so that detector 120 is rotatable about axis R in the directions indicated by double-headed arrow D.

X-ray source 110 and arm 132 are suitably weighted to provide a moment on the upper portion 211 of arm 132, i.e., the portion above axis R, which moment is greater than the moment of the lower portion 212 of arm 132, i.e., the portion below axis R. Desirably, when x-ray source 110 is positioned at a first or elevated upper position 201 (as shown in FIGS. 2 and 3), arm 132 and x-ray source 110 will tend to rotate about axis R so that x-ray source 110 moves along arc C to a second or lower position 202 (as shown in phantom in FIGS. 2 and 3).

In this exemplary embodiment, actuating system 140 comprises a hydraulic system having first and second hydraulic cylinders 142 and 144, respectively, a reservoir 160, a pump 170, and valves 172 and 174. Hydraulic cylinder 142 comprises a cylinder body 141 pivotally attached to support 131, and a piston 143 pivotally attachable at an upper end to one side of arm 132 for positioning x-ray source 110 relative to detector 120. Hydraulic cylinder 144 comprises a cylinder body 145 pivotally attached to support 131, and a piston 147 pivotally attachable at an upper end to the other side of arm support 132 for positioning x-ray source 110 relative to detector 120.

Reservoir 160, pump 170, and valves 172 and 174, are operably connected to hydraulic cylinders 142 and 144 so that fluid may be introduced into and removed from cylinder bodies 141 and 145 to position arm 132, and thus x-ray source 110 in an elevated position (e.g., position 201), relative to detector 120. Hydraulic cylinders 142 and 144 are suitably stabilized or maintained in a generally vertically disposed position when they are not attached to the respective sides of arm 132, or when apparatus 100 is operated to obtain standard cranial-caudal or medio-lateral oblique mammograms in which case, arm 132 and arm 134 may be suitably locked in a fixed position relative to support 131.

By way of example and not limitation, the x-ray source, the support, and the arms typically are of a type such as General Electric Medical Systems Model DMR Mammography System, and suitably modified as discussed above.

With reference to FIG. 2, the initial setup of apparatus 100 for obtaining tomosynthesis data is as follows. Desirably, x-ray detector arm 134, and thus detector 120, is disposed at a fixed angle B from vertical (shown by reference line Y in Figures); typically angle B is in the range between about 50 degrees to about 70 degrees from vertical for medio-lateral oblique views. When angle B has been selected, arm 134 is secured in place to prevent movement. Hydraulic cylinder 142 is attached to x-ray source arm 132. Pump 170 is energized to fill cylinder body 143 to elevate and position x-ray source 110 at an elevated position 201 as shown in FIG. 2, e.g., about +24 degrees from an axis L1 extending normal to detector 120.

An object to be imaged 102, such as a breast of a patient, is positioned between a compression paddle 122 and detector 120, and maintained in a stationary fixed position while x-ray source 110 is moved from the elevated position to a lower position 202 (shown in phantom) during which a plurality of images are obtained. The procedure is similar for obtaining images of the patient's other breast, but instead, hydraulic cylinder 144 is connected to arm 132 and motion of the arm is between the respective upper and lower positions 201 and 202 as illustrated in FIG. 3.

In one aspect of obtaining the plurality of images, valve 172 may be opened to drain fluid from cylinder body 141 to reservoir 160 so that x-ray source 110 descends smoothly under the influence of gravity from the elevated position 201 to the lower position 202. As used herein, "smooth descent" and the like refer to the x-ray source moving between respective radiating positions without intermediate stops and in a fashion that does not involve abrupt changes in acceleration. During the descent of x-ray source 110, a plurality, desirably between eight and fifteen, images are obtained by the x-ray source emitting radiation towards the object to be imaged and the detector. For example, use of six degree intervals, positions "a" through "i" shown in FIG. 2, result in obtaining nine images. Each position at which the source emits radiation towards the object to be imaged is a respective radiating position. The image obtained at each position by the detector desirably has a low radiation dose. The total radiation dose for all of the images is desirably equivalent to, or only higher by a medically insignificant amount than the radiation dose of a standard single view mammogram.

Apparatus 100 desirably includes a processor 150 for controlling actuator system, and processing a plurality of images obtained at a plurality of positions of x-ray source 110 relative to detector 120 as further described below.

For example, a suitable inclinometer 180 having a sensitivity of about +/−0.1 degree may be attached to arm 132 and coupled to processor 150. Processor 150 typically also is interfaced with x-ray source 110 to supply a signal for energizing x-ray source 110 at the appropriate positions, e.g., positions "a–j", as x-ray source descends from the elevated position 201 to lower position 202. Advantageously, apparatus 100 includes suitable shock absorbers such as springs, or pressurized reservoirs to bring arm 132 to decelerate arm 132 to a gentle stop at position 202; alternatively processor 150 is programmed to slowly close valve 172 to decelerate x-ray source 110 as it approaches its position 202 at the end of the scan.

In another aspect of obtaining the plurality of images, x-ray source 110 may be moved to come to a rest or stop at each of the appropriate positions, e.g., positions "a–i", at which time (when no longer in motion) x-ray source is energized for generating an exposure. For example, processor 150 typically is interfaced with inclinometer 180 and valve 172 to control the descent of and cause x-ray source to come to a rest at each of the desired positions, as well as supply a signal for energizing x-ray source 110 while x-ray source is stopped or stationarily maintained at each of the desired positions.

From the present invention, it will be appreciated by those skilled in the art that instead of an inclinometer, a linear encoder or similar device can be attached to the hydraulic cylinder and calibrated for providing angular measurements. Similarly, the encoder can be interfaced with the computer and used to control the position of the x-ray source.

Figure 4A:
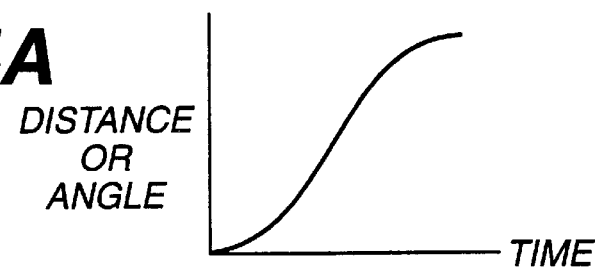
FIGS. 4A–4C are partial graphical illustrations of distance or angle, velocity, and acceleration, respectively, of the motion of the x-ray source, shown in FIGS. 2 and 3, over time during a procedure for obtaining tomographic data.
Figure 4B:
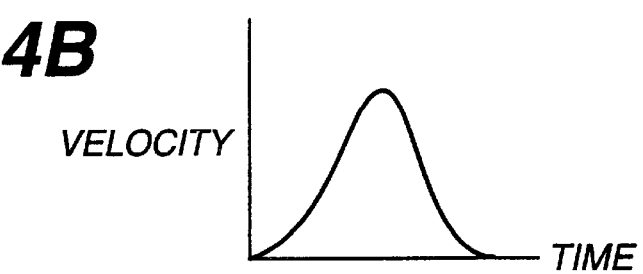
Figure 4C:
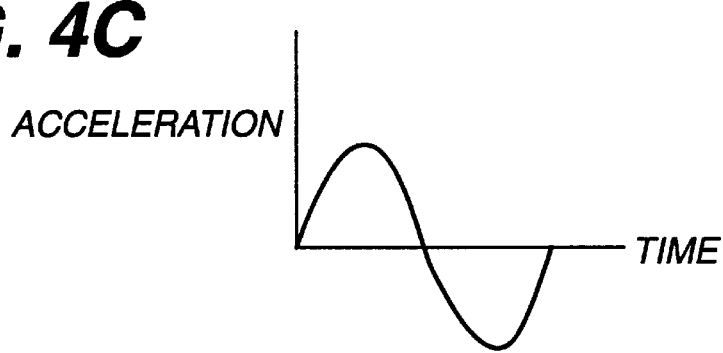

FIGS. 4A–4C graphically illustrate an explanary motion of x-ray source 110 which desirably results in a smooth transition from the upper or elevated position 201 to the lower or end position 202. FIG. 4A illustrates the change in distance or angle over time between the stop positions of the arm (e.g., positions 201 and 202). FIGS. 4B and 4C illustrate the change in velocity and acceleration, respectively, between the stop positions over time. Desirably, the accelerations and deceleration of x-ray source over time between the elevated position and the lower position is sinusoidal in nature to provide the desired smoothness in motion of the arm.

Figure 5:
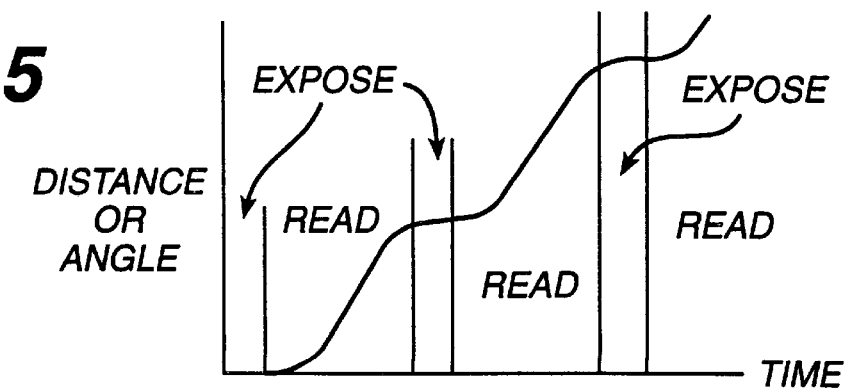
FIG. 5 is a graphical illustration similar to FIG. 4A which spans a period of time for obtaining a plurality of images.

Desirably, as shown in FIG. 5, the change in distance or angle between respective positions "a–j" over time for a plurality of positions results in x-ray source 110 being maintained in a fixed or stationary position at which time X-ray source is energized. The periods of time between the exposure allow the processor to read the digital detector. Advantageously, x-ray source is quickly and smoothly moved during the minimum time required for reading the detector.

In an alternative embodiment of the actuator, an intermediate pair of variable sized reservoirs may be used in the drain line from each of hydraulic cylinders so that the pair of reservoirs are alternately filled and emptied. The volume of each reservoir is desirably configured to contain an amount of fluid to be drained or removed from the hydraulic cylinder to permit x-ray source 110 to move from one position to the next. For example, when a reservoir is filled, the x-ray source can be energized to generate an exposure. The hydraulic cylinder would then be connected to the other reservoir to continue the scan, while the first would be emptied into the lower reservoir.

The hydraulic system and motion of the x-ray source allows for the acquisition of the tomosynthesis images in approximately three to five seconds which is sufficiently rapid enough to make the apparatus clinically applicable. The separate projection images obtained during the imaging procedure typically are processed for use by the operator by processor 150 or other readout modalities coupled to the detector.

Desirably, the plurality of separate projected images generated by apparatus 100 (x-ray source 110 located at positions "a–i") are shifted and added, e.g., transformed, to reconstruct one or more planes or slices S in the object imaged that are parallel to the plane of detector 120. Tomosynthesis allows reconstruction of "in-focus" tomographic planes or slices S at any level, e.g., at about 1.5 mm to about 3 mm spacing. Advantageously, the invention allows a physician or radiologist to see through "structured noise" of normal breast tissue to improve detection and characterization of breast cancer.

By way of example and not limitation, the generation of tomographic planes or slices S may be obtained by the processes disclosed in U.S. Pat. No. 5,872,828 to Niklason et al., or in Niklason et al, "Digital Tomosynthesis in Breast Imaging," Radiology, Vol. 205, pages 399–406, November 1997.

Processor 150 is typically a digital computer that is programmed to process imaging signals received from detector 120 during the x-ray procedure. An exemplary processor 150 may include a suitable computer (e.g., SPARC 20 workstation from Sun Microsystems PENTIUM based computer, etc.) having a hard, drive, input devices such as a keyboard, a mouse, magnetic storage media (e.g., tape cartridges or disks), optical storage media (e.g., CD-ROMs), and output devices such as a display and a printer. Suitable programming to perform the transformations, as explained in greater detail above, is installed or embedded in processor 150.

From the present description, it will be appreciated the apparatus may be configured to image a variety of objects, and is not limited to breast imaging. It will also be appreciated by those skilled in the art that pneumatic cylinders may be suitably employed in place of the hydraulic cylinders. With pneumatic cylinders, a reservoir would not be necessary.

Thus, while various embodiments of the present invention have been illustrated and described, it will be appreciated to those skilled in the art that many changes and modifications may be made thereunto without departing from the spirit and scope of the invention.

What is claimed is:

1. An apparatus for obtaining tomosynthesis data of an object, the apparatus comprising:

a radiation source;

a radiation detector;

an actuator operably connectable to said radiation source, said actuator operable to controllably allow said radiation source to move under the influence of gravity from a first position to a second position relative to said radiation detector; and wherein said radiation source is disposed to emit radiation at a plurality of radiating positions intermediate between said first position and said second position such that said radiation is emitted towards the object to be imaged and said radiation detector.

2. The apparatus of claim 1 wherein said actuator is operable to control movement of said radiation source so that said radiation source continuously moves from said first position to said second position.

3. The apparatus of claim 1 wherein said actuator is operable to control movement of said radiation source so that said radiation source stops at said plurality of radiating positions.

4. The apparatus of claim 3 wherein said actuator is operable to transition said radiation source between said plurality of radiating positions without stopping between adjacent ones of said radiating positions.

5. The apparatus of claim 4 wherein said actuator is operable to control movement of said radiation source from said first position to said second position so that acceleration of said radiation source varies generally sinusoidally between respective stop points of said radiation source.

6. The apparatus of claim 1, wherein said actuator comprises a processor operable to energize said radiation source at each of said plurality of radiating positions.

7. The apparatus of claim 1 further comprising a processor operable to generate, from detected radiation, a plurality of spaced-apart planar images through the object.

8. An apparatus for obtaining tomosynthesis data of an object, the apparatus comprising:

a radiation source;

a radiation detector;

a support;

an arm having a first end portion attached to said radiation source and a second end portion pivotally attached to said support so that said radiation source is movable along an arc;

an actuating system operably connectable to said arm to controllably allow said radiation source to move under the influence of gravity from at least one elevated position to at least one lower position relative to said radiation detector; and wherein said radiation source is disposed to emit radiation at a plurality of radiating positions intermediate between said first position and said second position such that said radiation is emitted towards the object to be imaged and said radiation detector.

9. The apparatus of claim 8 wherein said actuating system is a hydraulic system comprising a first hydraulic cylinder operably connectable to a first side of said arm for controllably allowing said radiation source to move under the influence of gravity from a first elevated position to a first lower position along said arc, and a second hydraulic cylinder being operably connectable to a second side of said arm for controllably allowing said radiation source to move under the influence of gravity from a second elevated position to a second lower position along said arc.

10. The apparatus of claim 8 wherein said hydraulic system comprises at least one hydraulic cylinder, and at least one valve operably connected to said at least one hydraulic cylinder for controllably discharging fluid from said at least one hydraulic cylinder so that said radiation source continuously moves from said at least one elevated position to said at least one lower position.

11. The apparatus of claim 10 further comprising a processor operable to generate, from detected radiation, a plurality of spaced-apart planar images through the object.

12. The apparatus of claim 10 wherein said hydraulic system comprises at least one hydraulic cylinder, and at least one valve operably connected to said at least one hydraulic cylinder for controllably draining fluid from said at least one hydraulic cylinder so that said radiation source stops at each of said plurality of radiating positions.

13. The apparatus of claim 12 wherein said at least one valve controllably drains fluid from said at least one hydraulic cylinder so that said radiation source smoothly transitions between said plurality of positions.

14. The apparatus of claim 8 wherein said actuating system comprises a pneumatic system.

15. The apparatus of claim 14, wherein said processor is operably connected to said at least one valve and to said radiation source for energizing said radiation source at said plurality of positions.

16. The apparatus of claim 8 wherein said radiation source comprises an x-ray tube and said radiation detector comprises a digital x-ray detector.

17. A method for obtaining tomosynthesis data of an object, the method comprising:

positioning a radiation source in an elevated position with the object disposed between the radiation source and a radiation detector;

irradiating the object with radiation at a plurality of radiating positions as the radiation source is allowed to move under the influence of gravity from an elevated position to a lower position; and detecting radiation passing through the object at the plurality of radiating positions with the radiation detector.

18. The method of claim 17 further comprising controlling movement of the radiation source so that the radiation source continuously moves from the elevated position to the lower position.

19. The method of claim 17 further comprising controlling movement of the radiation source so that the radiation source stops at each of the plurality of radiating positions.

20. The method of claim 19 wherein controlling movement of the radiation source comprises smoothly transitioning the radiation source between each of the plurality of positions.

21. The method of claim 20 wherein controlling movement of the radiation source comprises varying the acceleration over time of the radiation source in conformance with a generally sinusoidal curve.

22. The method of claim 20 wherein the irradiating object generally corresponds to a period of time of the stops and the detecting radiation passing through the object generally corresponds to a period of time between the stops.

23. The method of claim 17 further comprising generating, from the detected radiation passing through the object at each of the plurality of positions, a plurality of spaced-apart planar images through the object.

24. The method of claim 17 further comprising positioning the radiation detector in a generally fixed medio-lateral oblique orientation.

* * * * *